United States Patent [19]

Sih

[11] 4,255,339

[45] Mar. 10, 1981

[54] 19-HYDROXY-19-METHYL-6-ALKOXY-PGI$_1$ COMPOUNDS

[75] Inventor: John C. Sih, Portage, Mich.

[73] Assignee: The Upjohn Company, Kalamazoo, Mich.

[21] Appl. No.: 126,507

[22] Filed: Mar. 3, 1980

Related U.S. Application Data

[62] Division of Ser. No. 54,720, Jul. 5, 1979, Pat. No. 4,225,507.

[51] Int. Cl.$^3$ .......................................... C07D 307/935
[52] U.S. Cl. .......................... 260/346.22; 260/346.73; 548/252; 548/253
[58] Field of Search ...................... 260/346.22, 346.73; 548/252, 253

[56] References Cited

PUBLICATIONS

Johnson et al., Prostaglandins, 12, pp. 915–928 (1976).

*Primary Examiner*—Henry R. Jiles
*Assistant Examiner*—Bernard Dentz
*Attorney, Agent, or Firm*—Robert A. Armitage

[57] ABSTRACT

The present invention provides novel 19-hydroxy-19-methyl-6-alkoxy-PGI$_1$ compounds which are useful for pharmacological purposes, e.g., anti-asthmatic indications.

5 Claims, No Drawings

19-HYDROXY-19-METHYL-6-ALKOXY-PGI$_1$ COMPOUNDS

CROSS REFERENCE TO RELATED APPLICATION

The present invention is a divisional application of U.S. Ser. No. 054,720, filed 5 July 1979 now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 19-hydroxy-19-methyl-6-alkoxy-PGI$_1$ compounds. The novel prostacyclin analogs are useful for pharmacological purposes, e.g., as anti-asthmatic agents. The preparation and use of these compounds is incorporated here by reference from U.S. Pat. No. 4,225,507.

Prior Art

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides a prostacyclin-type compound of the formula

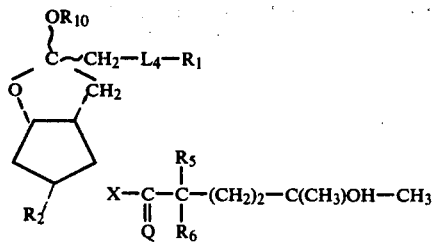

wherein
L$_4$ is
(1) —(CH$_2$)$_n$—, wherein n is one to 5, inclusive, or
(2) —(CH$_2$)$_p$—CF$_2$—, wherein p is 2, 3, or 4,
wherein
R$_{10}$ is straight-chain alkyl of one to 6 carbon atoms, inclusive;
wherein
Q is oxo, α—H:β—H, α—OH:β—R$_4$, or α—R$_4$:β—OH,
wherein
R$_4$ is hydrogen or alkyl of one to 4 carbon atoms, inclusive,
wherein
R$_1$ is
(1) —COOR$_3$,
(2) —CH$_2$OH,
(3) —CH$_2$N(R$_7$)(R$_8$),
(4) —CO—N(R$_7$)(R$_8$),
(5) —CO—NH—SO$_2$—R$_{15}$, or
(6) tetrazolyl,
wherein
R$_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive:
(g) —(p-Ph)—CO—CH$_3$,
(h) —(p-Ph)—NH—CO—(p-Ph)—NH—CO—CH$_3$,
(i) —(p-Ph)—NH—CO—(Ph),
(j) —(p-Ph)—NH—CO—CH$_3$,
(k) —(p-Ph)—NH—CO—NH$_2$,
(l) —(p-Ph)—CH=N—NH—CO—NH$_2$,
(m) β-naphthyl,
(n) —CH$_2$—CO—R$_{16}$,
wherein
—(p-Ph)— is para-phenylene and -(Ph) is phenyl;
wherein
R$_{16}$ is phenyl, p-bromophenyl, p-biphenylyl, p-nitrophenyl, p-benzamidophenyl, or 2-naphthyl, or
(o) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive,
wherein
R$_2$ is hydrogen, hydroxyl, or hydroxymethyl,
wherein
R$_5$ and R$_6$ are hydrogen, alkyl of one to 4 carbon atoms, inclusive, or fluoro, being the same or differnt, with the proviso that one of R$_5$ and R$_6$ is fluoro only when the other is hydrogen or fluoro, and
wherein
X is
(1) trans—CH=CH—,
(2) cis—CH=CH—,
(3) —C≡C—, or
(4) —CH$_2$CH$_2$—.

DESCRIPTION OF THE PREFERRED EMBODIMENTS

The present invention particularly relates to the following compounds:

2-Decarboxy-2-hydroxymethyl-9-deoxy-6ε,9α-epoxy-6ε-methoxy-19-hydroxy-19-methyl-PGF$_1$, and 2-Decarboxy-2-hydroxymethyl-9-deoxy-6ε,9α-epoxy-6ε-methoxy-16,16-difluoro-19-hydroxy-19-methyl-PGF$_1$.

I claim:

1. A prostacyclin-type compound of the formula

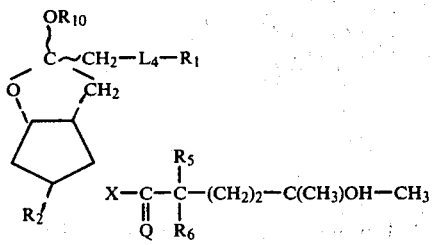

wherein

L₄ is
(1) —(CH$_2$)$_n$—, wherein n is one to 5, inclusive, or
(2) —(CH$_2$)$_p$—CF$_2$—, wherein p is 2, 3, or 4, wherein R$_{10}$ is straight-chain alkyl of one to 6 carbon atoms, inclusive;

wherein

Q is oxo, α—H:β—H, α—OH:β—R$_4$, or α—R$_4$:ε—OH, wherein

R$_4$ is hydrogen or alkyl of one to 4 carbon atoms, inclusive, wherein

R$_1$ is
(1) —COOR$_3$,
(2) —CH$_2$OH,
(3) —CH$_2$N(R$_7$)(R$_8$),
(4) —CO—N(R$_7$)(R$_8$),
(5) —CO—NH—SO$_2$—R$_{15}$, or
(6) tetrazolyl, wherein R$_3$ is
(a) hydrogen,
(b) alkyl of one to 12 carbon atoms, inclusive,
(c) cycloalkyl of 3 to 10 carbon atoms, inclusive,
(d) aralkyl of 7 to 12 carbon atoms, inclusive,
(e) phenyl,
(f) phenyl substituted with one, 2, or 3 chloro or alkyl groups of one to 3 carbon atoms, inclusive;
(g) —(p-Ph)—CO—CH$_3$,
(h) —(p-Ph)—NH—CO—(p-Ph)—NH—CO—CH$_3$,
(i) —(p-Ph)—NH—CO—(Ph),
(j) —(p-Ph)—NH—CO—CH$_3$,
(k) —(p-Ph)—NH—CO—NH$_2$,
(l) —(p-Ph)—CH=N—NH—CO—NH$_2$,
(m) β-naphthyl,
(n) —CH$_2$—CO—R$_{16}$, wherein
—(p-Ph)— is para-phenylene and —(Ph) is phenyl;

wherein
R$_{16}$ is phenyl, p-bromophenyl, p-biphenylyl, p-nitrophenyl, p-benzamidophenyl, or 2-naphthyl, or (o) a pharmacologically acceptable cation; wherein R$_7$ and R$_8$ are hydrogen, alkyl of one to 12 carbon atoms, inclusive, benzyl, or phenyl, being the same or different, and wherein R$_{15}$ is hydrogen, alkyl of one to 12 carbon atoms, inclusive, phenyl, phenyl-substituted with one, 2, or 3 chloro or alkyl groups of one to 3 carbon atoms, inclusive, or phenyl substituted with hydroxycarbonyl or alkoxycarbonyl of one to 4 carbon atoms, inclusive, wherein
R$_2$ is hydrogen, hydroxyl, or hydroxymethyl, wherein
R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro, and wherein
X is
(1) trans—CH=CH—,
(2) cis—CH=CH—,
(3) —C≡C—, or
(4) —CH$_2$CH$_2$—.

2. A compound according to claim 1, wherein R$_1$ is —CH$_2$OH.

3. A compound according to claim 2, wherein L$_4$ is —(CH$_2$)$_3$, Q is α—OH:β—H, R$_2$ is hydroxyl, and X is trans—CH=CH—, and R$_{10}$ is methyl.

4. 2-Decarboxy-2-hydroxymethyl-9-deoxy-6ε,9α-epoxy-6ε-methoxy-19-hydroxy-19-methyl-PGF$_1$, a compound according to claim 3.

5. 2-Decarboxy-2-hydroxymethyl-9-deoxy-6ε,9α-epoxy-6ε-methoxy-16,16-difluoro-19-hydroxy-19-methyl-PGF$_1$, a compound according to claim 3.

* * * * *

UNITED STATES PATENT OFFICE
CERTIFICATE OF CORRECTION

Patent No. 4,255,339                     Dated     10 March 1981

Inventor(s)   John C. Sih

It is certified that error appears in the above-identified patent and that said Letters Patent are hereby corrected as shown below:

Column 1, lines 42-53, and Column 3, lines 1-12, the formula should read as follows instead of as appears in the printed patent:

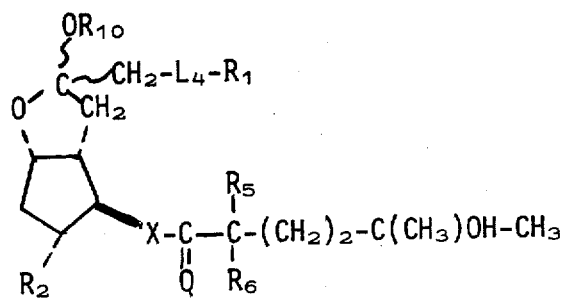

Column 3, lines 20-21, "$\alpha$-$R_4$:$\epsilon$-OH" should read -- $\alpha$-$R_4$:$\beta$-OH --.

Signed and Sealed this

Second Day of June 1981

[SEAL]

Attest:

RENE D. TEGTMEYER

Attesting Officer    Acting Commissioner of Patents and Trademarks

UNITED STATES PATENT OFFICE
CERTIFICATE OF CORRECTION

Patent No. 4,255,339            Dated  10 March 1981

Inventor(s)  John C. Sih

It is certified that error appears in the above-identified patent and that said Letters Patent are hereby corrected as shown below:

Column 3, lines 1-10, that portion of the formula reading

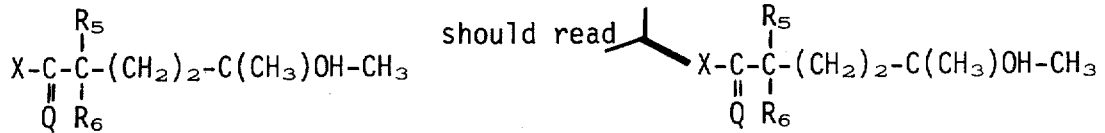

Column 3, line 21, ":ε-OH," should read -- :β-OH, --;
Column 4, lines 38-39 and lines 41-42, "-6ε,9α-epoxy-6ε-methoxy-" should read -- -6ξ,9α-epoxy-6ξ-methoxy- --.

Signed and Sealed this

Twenty-first Day of July 1981

[SEAL]

*Attest:*

*Attesting Officer*

GERALD J. MOSSINGHOFF

*Commissioner of Patents and Trademarks*